United States Patent
Scheenstra et al.

(10) Patent No.: US 10,080,694 B1
(45) Date of Patent: *Sep. 25, 2018

(54) HARNESS SYSTEM FOR PATIENT TRANSPORT APPARATUS

(71) Applicant: Stryker Corporation, Kalamazoo, MI (US)

(72) Inventors: Levi Scheenstra, Plainwell, MI (US); Tyler Ethen, Portage, MI (US); Roy E. Holmberg, III, Portage, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/595,416

(22) Filed: May 15, 2017

Related U.S. Application Data

(63) Continuation of application No. 15/497,693, filed on Apr. 26, 2017.

(51) Int. Cl.
| | | |
|---|---|---|
| *A61G 1/044* | (2006.01) | |
| *A61G 1/04* | (2006.01) | |
| *A61F 5/37* | (2006.01) | |

(52) U.S. Cl.
CPC .............. *A61G 1/044* (2013.01); *A61G 1/04* (2013.01); *A61F 5/3769* (2013.01); *A61F 5/3776* (2013.01)

(58) Field of Classification Search
CPC . A61G 1/00; A61G 1/01; A61G 1/013; A61G 1/04; A61G 1/044; A61G 1/048; A61G 7/015; A61G 7/0149; A61G 7/1051; A61G 7/1049; A61F 5/37; A61F 5/3707; A61F 5/3769; A61F 5/3776; A61F 5/3784
USPC ... 5/628, 625, 627, 88.1, 85.1, 83.1, 81.1 R; 128/869, 870, 875, 876
See application file for complete search history.

(56) References Cited

U.S. PATENT DOCUMENTS

| | | |
|---|---|---|
| 3,970,329 A | 7/1976 | Lewis |
| 6,007,092 A | 12/1999 | Martz |
| 6,740,607 B2 | 5/2004 | Veiga et al. |
| 7,389,552 B1 | 6/2008 | Reed et al. |
| 7,398,571 B2 | 7/2008 | Souke et al. |
| 7,905,233 B2 | 3/2011 | Hopper |
| 8,434,827 B2 | 5/2013 | Young et al. |
| 8,615,829 B2 * | 12/2013 | Kenalty .......... A61G 1/02 5/628 |
| 9,757,286 B2 * | 9/2017 | Beaulieu .......... A61G 1/01 |
| 2002/0105176 A1 | 8/2002 | Hammer et al. |
| 2008/0168603 A1 | 7/2008 | Ayette et al. |

(Continued)

OTHER PUBLICATIONS

Article entitled "Medical Application for Biothane Coated Webbing" from the website biothane.us; https://www.biothane.us/applications/medical/.

(Continued)

*Primary Examiner* — Robert G Santos
(74) *Attorney, Agent, or Firm* — Howard & Howard Attorneys PLLC

(57) ABSTRACT

A harness system for a patient transport apparatus. The harness system comprises one or more harness assemblies. Each harness assembly comprises a flexible restraint member formed of a coated fabric and comprising one or more joints in which stitches join sections of the coated fabric. Covers are attached to the coated fabric over the stitches to provide a barrier to outside contaminants and to ease cleaning of the flexible restraint member.

20 Claims, 14 Drawing Sheets

(56) References Cited

U.S. PATENT DOCUMENTS

| | | | | |
|---|---|---|---|---|
| 2010/0064432 | A1* | 3/2010 | Duquette | A61G 7/1015 5/88.1 |
| 2012/0151679 | A1* | 6/2012 | Kenalty | A61G 1/02 5/628 |
| 2014/0259391 | A1* | 9/2014 | Karlsson | A61G 7/1073 5/85.1 |
| 2015/0143634 | A1* | 5/2015 | Beaulieu | A61G 1/01 5/626 |
| 2016/0000625 | A1* | 1/2016 | Duquette | A61G 7/1015 5/88.1 |

OTHER PUBLICATIONS

SAE J3027 Explained, The Stryker Solution, Stryker Brochure dated Nov. 6, 2014; 3 pages, McCoy Miller.

Dick Medical Supply 2016/2017 Product Catalog, 24 pages.

Ferno Model 417-1 Series Harness Restraint Brochure dated Sep. 2013; 4 pages, Ferno-Washington, Inc.

Stryker Power-PRO XT Ref 6506 Operations/Maintenance Manual; 67 pages, Stryker Medical, published at least by Apr. 25, 2017.

Chest Restraint Shoulder Harness, BioThane G1, Yellow, for Stryker 6500; https://www.boundtree.com/3175-67025-chest-restraint-product-38475-181.aspx?search=3175-67025.

Biothane Product Data Brochure, 8 pages, bioplastics.us, published at least by Apr. 25, 2017.

Stryker X-Restraint Cot Straps instructional Video, posted Feb. 29, 2016 by Ettore Dimiceli; URL: https://www.youtube.com/watch?v=9sZFDvWBLig.

How to Sew Biothane 1 instructional video, posted Sep. 22, 2016 by BioThane Coated Webbing; URL: https://www.youtube.com/watch?v=9KQZFIQb-il.

How to Sew Biothane 2 instructional video, posted Sep. 23, 2016 by BioThane Coated Webbing; URL: https://www.youtube.com/watch?v=exyrEj-7QGI.

Masson Inc., "PathoShield(R) Coated Webbing" and "PathoShield(R) Welds", URL: http://www.massoninc.com/pathoshield.php.

Masson Inc., "PathoShield(R) Coated Webbing" and "PathoShield(R) Welds", extracted from web.archive.org, published at least as early as Apr. 26, 2017; 2 pages.

* cited by examiner

HARNESS SYSTEM FOR PATIENT TRANSPORT APPARATUS

CROSS-REFERENCE TO RELATED APPLICATION

This application is a continuation of U.S. patent application Ser. No. 15/497,693, filed on Apr. 26, 2017, the disclosure of which is hereby incorporated by reference in its entirety.

BACKGROUND

Patient transport apparatuses facilitate care of patients in a health care setting. Patient transport apparatuses comprise, for example, hospital beds, stretchers, cots, wheelchairs, and chairs. A conventional patient transport apparatus comprises a support structure having a base, a support frame, and a patient support surface upon which the patient is supported.

In some cases, a patient transport apparatus is needed to transport a patient to a hospital or other emergency medical facility in an emergency vehicle. During transport, it is desirable for the patient to be safely and securely restrained to the patient transport apparatus for their own safety and the safety of emergency medical personnel or other people within the emergency vehicle.

A harness system may be used to secure the patient to the patient transport apparatus. It is desirable for the harness system to be of suitable strength to withstand certain crash events. Conventional harness systems, however, comprise polyester webbing that may be difficult to clean when dirt, grease, body fluids, and/or other contaminants are trapped in the webbing. Typically, such harness systems are discarded once they reach an undesirable, soiled condition.

A harness system designed to address and/or overcome one or more of the aforementioned challenges is desired.

DETAILED DESCRIPTION

Figure 1:
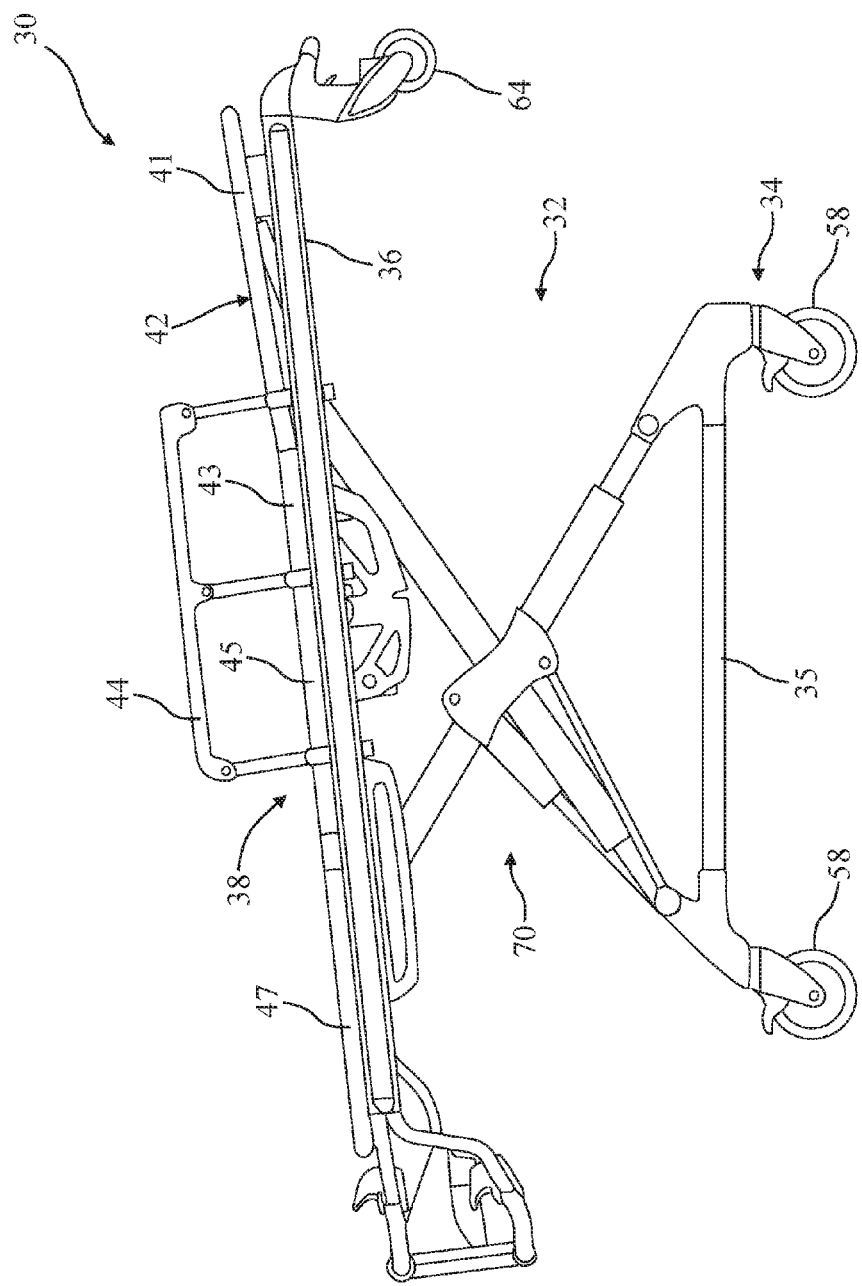
FIG. 1 is a side view of a patient transport apparatus.

Referring to FIG. 1, a patient transport apparatus 30 is shown for supporting a patient in a health care setting. The patient transport apparatus 30 may comprise a hospital bed, stretcher, cot, wheelchair, chair, or similar apparatus utilized in the care of a patient. In the embodiment shown in FIG. 1, the patient transport apparatus 30 comprises a cot that is utilized to transport patients in an emergency vehicle (e.g., an ambulance), such as from an emergency site to a hospital or other emergency medical facility.

The patient transport apparatus 30 shown in FIG. 1 comprises a support structure 32 that provides support for the patient. The support structure 32 comprises a base 34 and a support frame 36. The base 34 comprises a base frame 35. The support frame 36 is spaced above the base frame 35. The support structure 32 also comprises a patient support deck 38 disposed on the support frame 36. The patient support deck 38 comprises several sections, some of which are capable of articulating relative to the support frame 36, such as a back section 41, a seat section 43, a leg section 45, and a foot section 47. The patient support deck 38 provides a patient support surface 42 upon which the patient is supported.

The base 34, support frame 36, patient support deck 38, and patient support surface 42 each have a head end and a foot end corresponding to designated placement of the patient's head and feet on the patient transport apparatus 30. The construction of the support structure 32 may take on any known or conventional design, and is not limited to that specifically set forth above. In addition, a mattress (not shown) may be provided in certain embodiments, such that the patient rests directly on a patient support surface of the mattress while also being supported by the patient support surface 42.

Side rails 44 are coupled to the support frame 36 and thereby supported by the base 34. If the patient transport apparatus 30 is a hospital bed there may be more side rails. The side rails 44 may be fixed to the support frame 36 or may be movable between a raised position in which they block ingress and egress into and out of the patient transport apparatus 30, one or more intermediate positions, and a lowered position in which they are not an obstacle to such ingress and egress. In still other configurations, the patient transport apparatus 30 may not include any side rails.

Wheels 58 are coupled to the base 34 to facilitate transport over floor surfaces. The wheels 58 are arranged in each of four quadrants of the base 34 adjacent to corners of the base frame 35. In the embodiment shown, the wheels 58 are caster wheels able to rotate and swivel relative to the support structure 32 during transport. Each of the wheels 58 forms part of a caster assembly. Each caster assembly is mounted to the base 34. It should be understood that various configurations of the caster assemblies are contemplated. In addition, in some embodiments, the wheels 58 are not caster wheels and may be non-steerable, steerable, non-powered, powered, or combinations thereof. Additional wheels are also contemplated. For example, the patient transport apparatus 30 may comprise four non-powered, non-steerable wheels, along with one or more powered wheels.

A pair of loading wheels 64 (only one shown in FIG. 1) may be coupled to the support frame 36 to assist with loading of the patient transport apparatus 30 into the emergency vehicle and unloading of the patient transport apparatus 30 out of the emergency vehicle. In the embodiment shown, the loading wheels 64 are arranged nearer the head end than the foot end, but the loading wheels 64 may be placed in other locations to facilitate loading and/or unloading of the patient transport apparatus 30 into and out of the emergency vehicle, or for other purposes.

A lift device 70 is configured to raise and lower the patient support surface 42 between minimum and maximum heights relative to the floor surface and intermediate heights therebetween. The lift device 70 may be configured to operate in the same manner or a similar manner as the lift mechanisms shown in U.S. Pat. No. 7,389,552 or U.S. Pat. No. 7,398,571, both of which are hereby incorporated by reference in their entirety.

Figure 2:
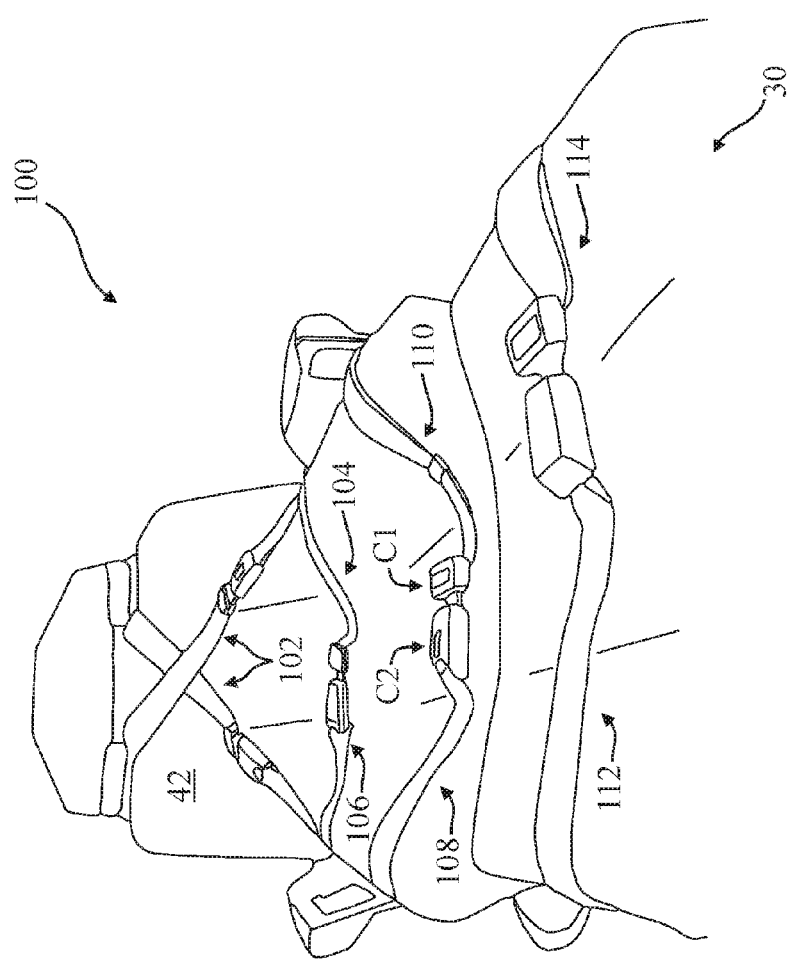
FIG. 2 is a front view of the patient transport apparatus illustrating a harness system.
Figure 3A:
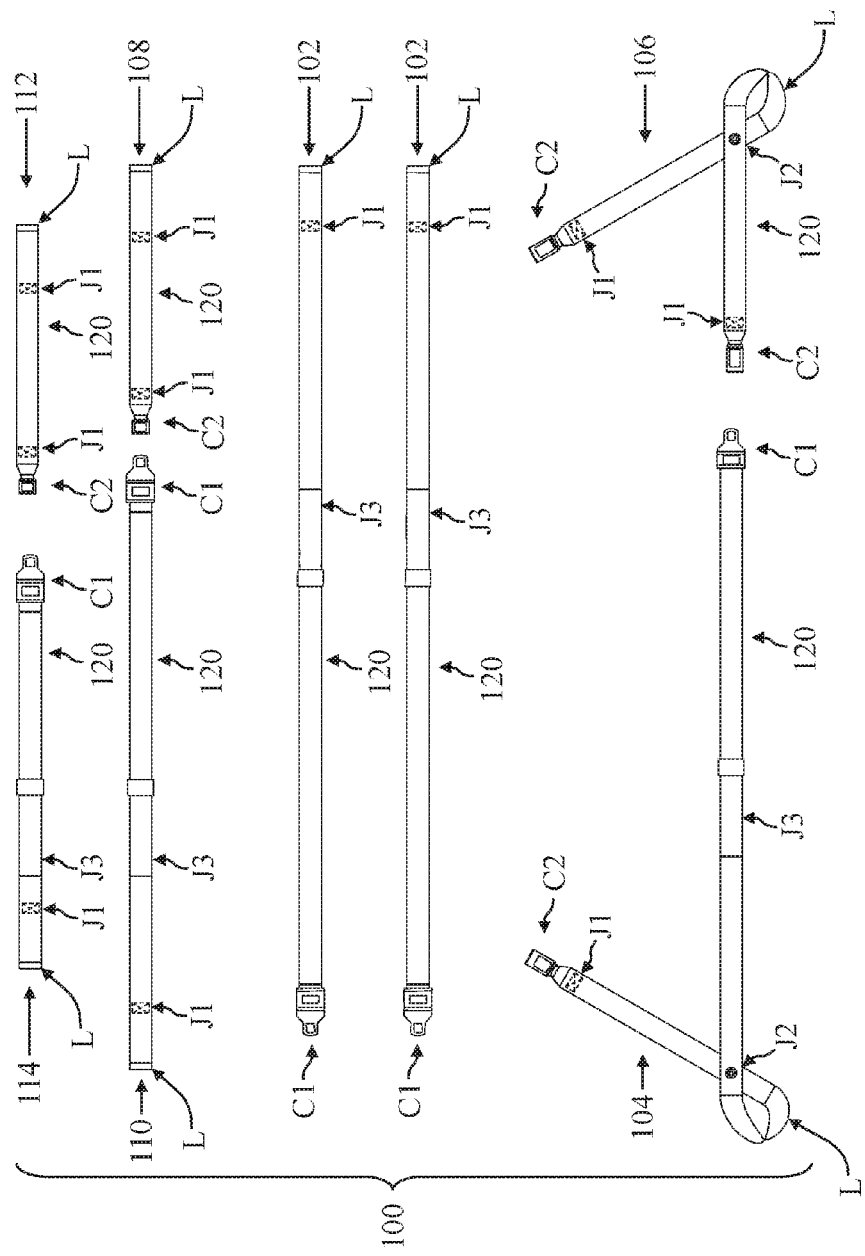
FIG. 3A is a top view of the harness system.
Figure 3B:
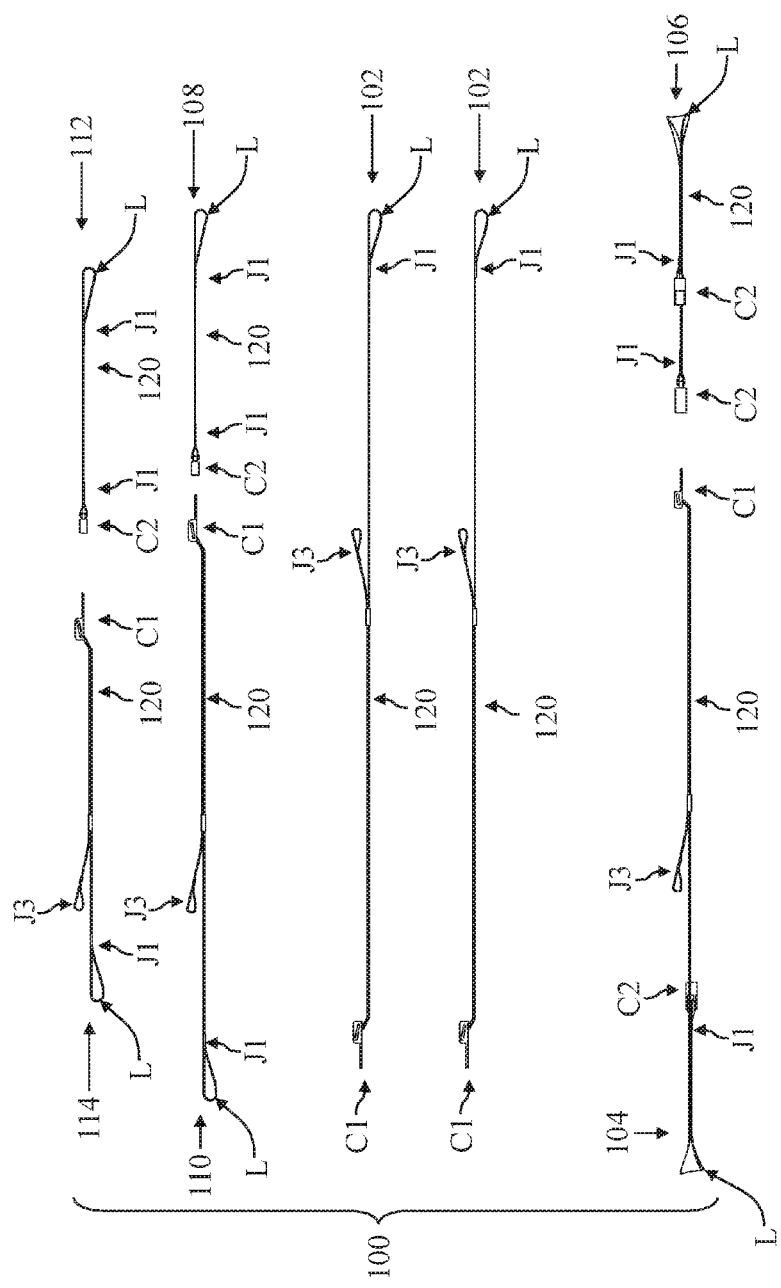
FIG. 3B is side view of the harness system.

Referring to FIGS. 2-3B, a harness system 100 is employed on the patient transport apparatus 30 to secure the patient on the patient support surface 42. The harness system 100 comprises one or more harness assemblies (also referred to as restraints) that cooperate to secure the patient to the patient transport apparatus 30. For instance, in the embodiment shown, the harness system 100 comprises shoulder harness assemblies 102, connecting harness assemblies 104, 106 that connect to the shoulder harness assemblies 102 and to each other, thigh harness assemblies 108, 110, and ankle harness assemblies 112, 114.

Figure 2A:
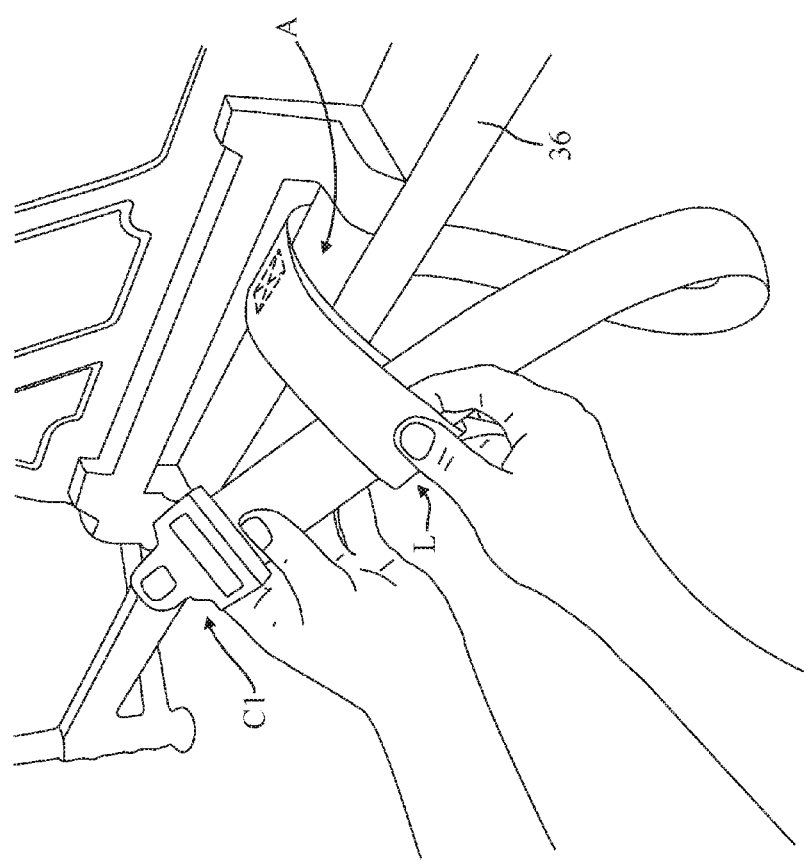
FIG. 2A is an illustration of securing a harness assembly of the harness system to a support frame.

Each of the harness assemblies 102-114 are configured to be attached to the support frame 36 and/or the patient support deck 38, but could be attached at any suitable location on the patient transport apparatus 30. In the embodiment shown, referring to FIG. 2A, each of the harness assemblies 102-114 comprises a connecting loop L that can be utilized to attach the harness assemblies 102-114. For instance, the connecting loop L may be passed through an opening at an anchor location A on the patient support deck 38 and/or the support frame 36 and a remainder of the harness assembly 102-114 can be passed through the connecting loop L to form a secure connection to the patient transport apparatus 30 at the anchor location A.

Referring to FIG. 2, the shoulder harness assemblies 102 are configured to be secured to the patient support deck 38 and/or the support frame 36 and placed over the patient's shoulders to form an X-shaped pattern across the patient's torso. As shown in FIGS. 3A and 3B, each of the shoulder harness assemblies 102 comprises a connecting loop L at one end and a connector C1. In the embodiment shown, the connectors C1 on the shoulder harness assemblies 102 comprise male insertion latches (e.g., tongues) configured to be received in connectors C2, such as buckles, for releasably locking to the buckles (similar to seatbelt buckles on vehicles). The connectors C1, C2 may be latches, buckles, catches, carabiners, or other suitable connectors for connecting the shoulder harness assemblies 102 to the connecting harness assemblies 104, 106, or to connect any two of the harness assemblies 102-114 together, as described herein.

The connecting harness assemblies 104, 106 are configured to be secured to the patient support deck 38 and/or the support frame 36. Each of the connecting harness assemblies 104, 106 comprises a connecting loop L and a pair of connectors C1 and/or C2 so that the connecting harness assemblies 104, 106 can be connected to the shoulder harness assemblies 102 and to each other. In the embodiment shown, the connectors C1, C2 on first connecting harness assembly 104 comprise an insertion latch and a buckle. The buckle is configured to releasably receive the insertion latch on one of the shoulder harness assemblies 102. The connectors C2 on second connecting harness assembly 106 comprise two buckles. One buckle is configured to releasably receive the insertion latch on the other shoulder harness assembly 102 and another buckle is configured to releasably receive the insertion latch on the first connecting harness assembly 104 to be secured across a waist of the patient.

The thigh harness assemblies 108, 110 are configured to be secured to the patient support deck 38 and/or the support frame 36 and connect to each other across thighs of the patient. Each of the thigh harness assemblies 108, 110 comprises a connecting loop L and a connector C1 or C2. In the embodiment shown, the connector C2 on first thigh harness assembly 108 comprises a buckle and the connector C1 on second thigh harness assembly 110 comprises an insertion latch configured to releasably engage the buckle.

The ankle harness assemblies 112, 114 are configured to be secured to the patient support deck 38 and/or the support frame 36 and connect to each other across ankles of the patient. Each of the ankle harness assemblies 112, 114 comprises a connecting loop L and a connector C1 or C2. In the embodiment shown, the connector C2 on first ankle harness assembly 112 comprises a buckle and the connector C1 on second ankle harness assembly 114 comprises an insertion latch configured to releasably engage the buckle.

Figure 4:
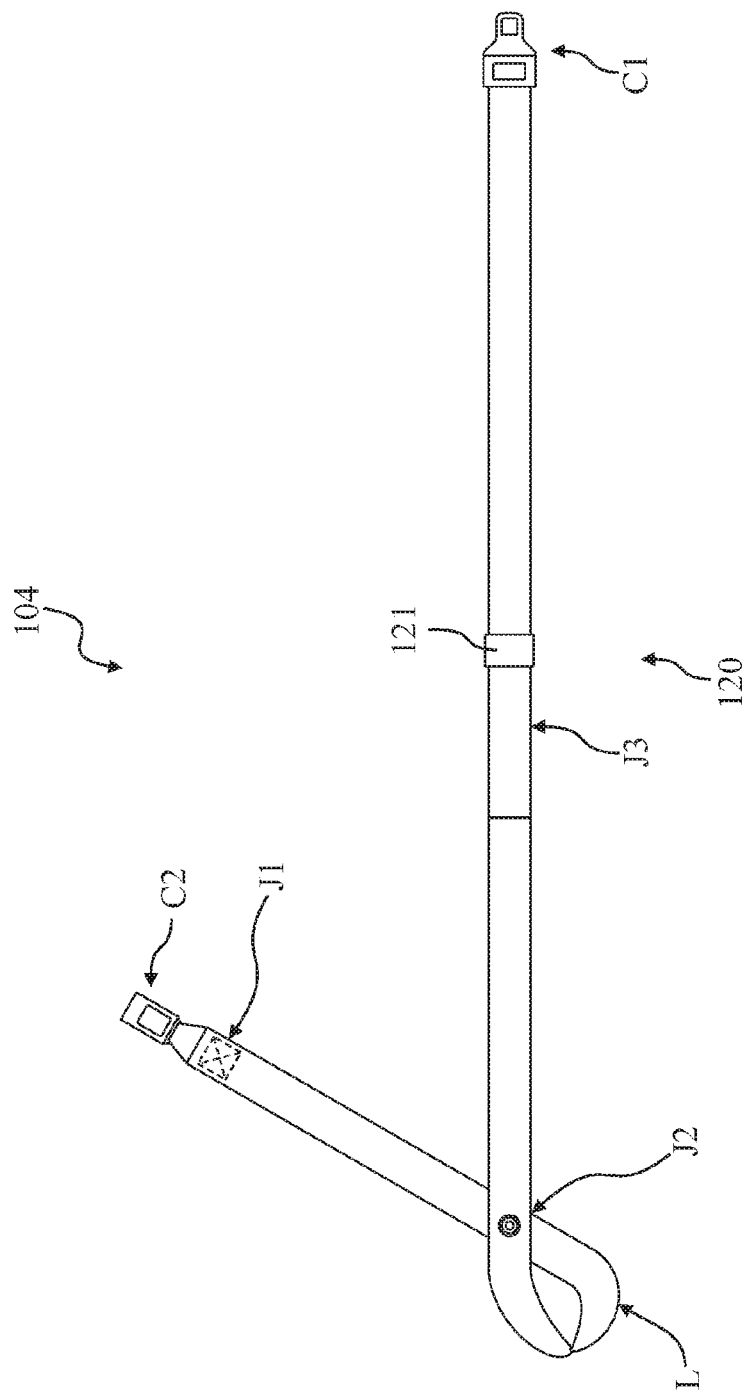
FIG. 4 is a top view of a harness assembly of the harness system.
Figure 5:
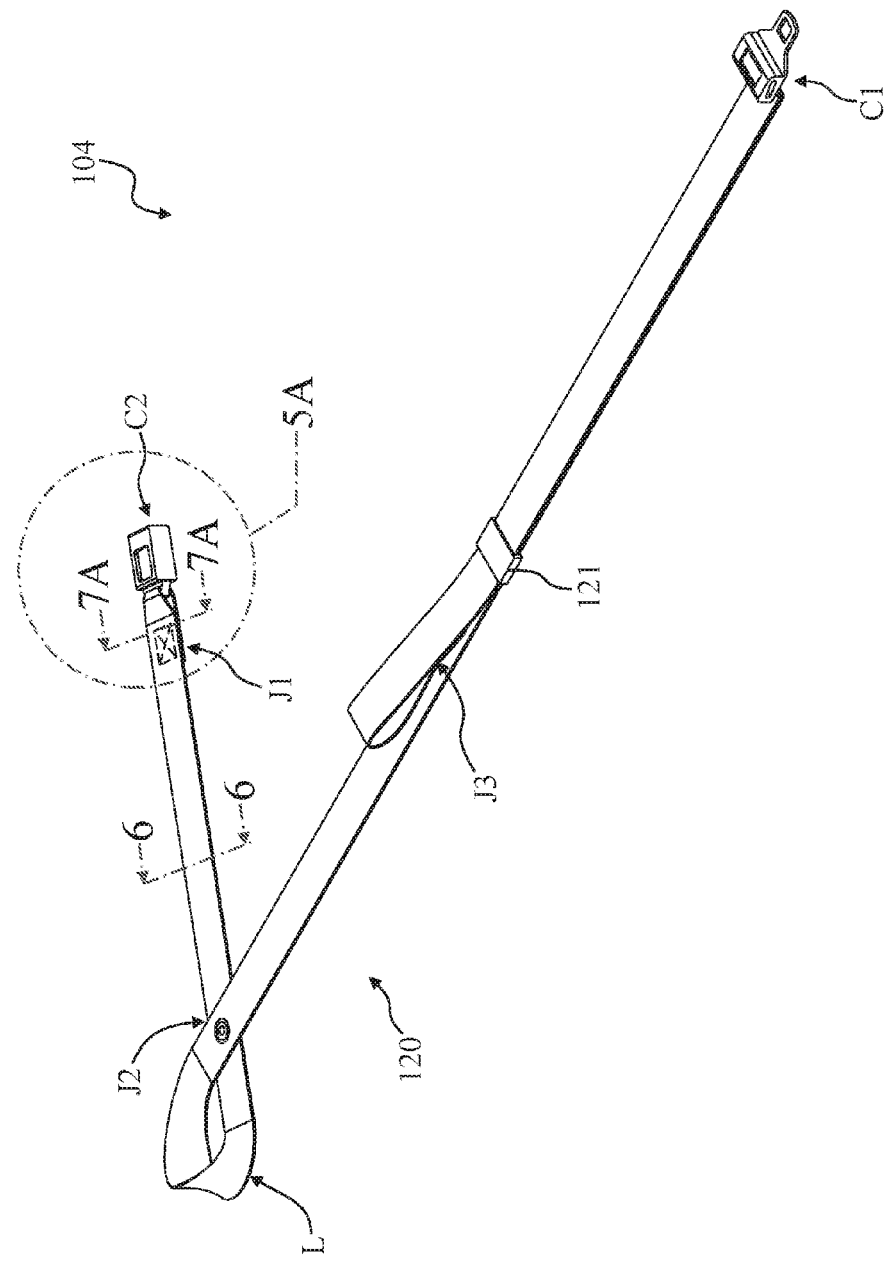
FIG. 5 is a top perspective view of the harness assembly of FIG. 4.

Referring to FIGS. 4 and 5, the first connecting harness assembly 104 is shown in more detail. Although reference is made primarily to the first connecting harness assembly 104, the description that follows is similarly applicable to the other harness assemblies, including the description of the materials forming the harness assemblies 102-114 and the manner in which joints are formed in the harness assemblies 102-114 to secure the connectors C1, C2 and/or to seal components of the harness assemblies 102-114 from contamination.

Figure 5A:
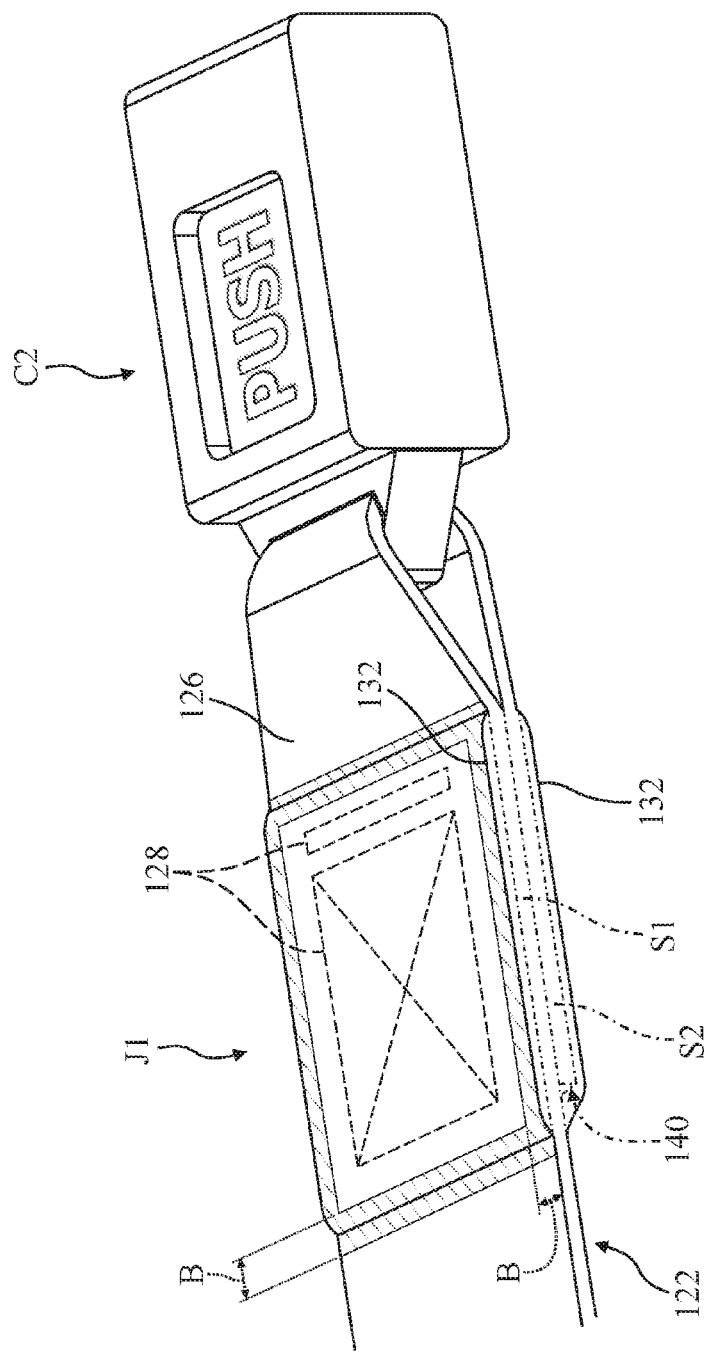
FIG. 5A is a close-up view of a joint of the harness assembly of FIG. 4.

The first connecting harness assembly 104 comprises an elongate flexible restraint member 120 that attaches to the connectors C1, C2. The flexible restraint member 120 comprises first, second, and third joints J1, J2, J3. The first joint J1, a close-up of which is shown in FIG. 5A, creates a loop to which the connector C2 is attached, such as the buckle. In some cases, the connector C2 is attached prior to forming the joint J1. The second joint J2 forms the connecting loop L previously described. The third joint J3 is formed to seal a free end in the manner described below and to prevent the free end from sliding through a retainer 121 used to facilitate adjustment of an operative length of the first connecting harness assembly 104 between the second joint J2 and the connector C1.

Figure 6:
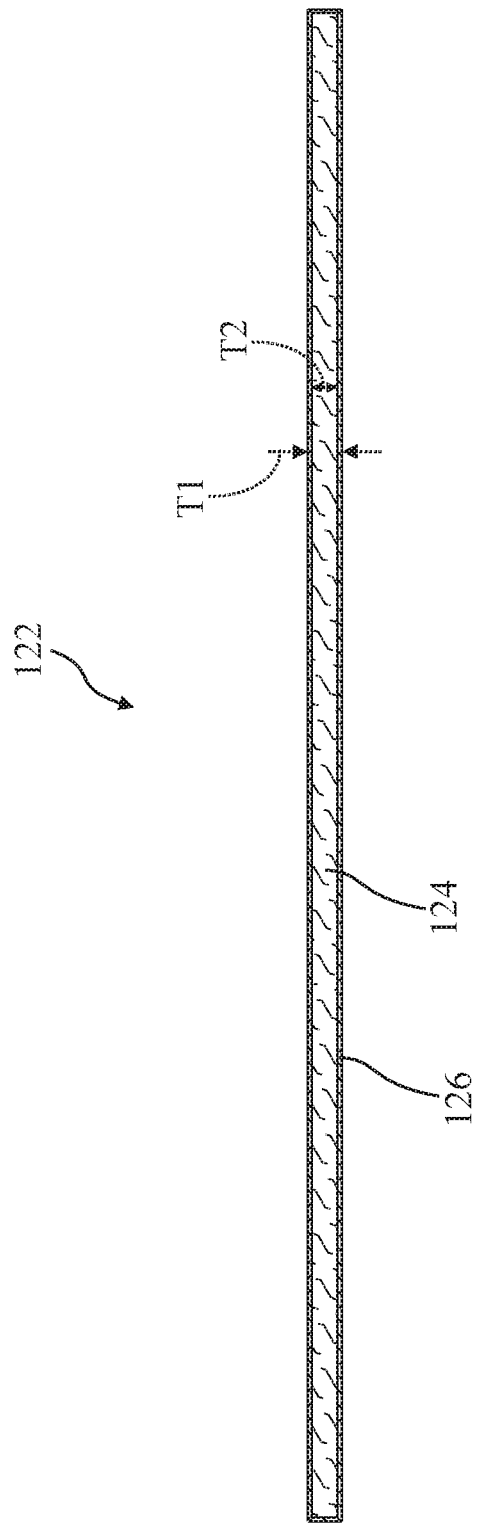
FIG. 6 is a cross sectional view of a flexible restraint member of the harness assembly taken along line 6-6 of FIG. 5.

FIG. 6 is a slice cross-sectional view through the flexible restraint member 120 outside of the first joint J1. The flexible restraint member 120 comprises coated fabric 122. In the embodiment shown, a single, continuous belt/strap of coated fabric 122 is provided to create the flexible restraint member 120. Multiple belts/straps, connected together, could be employed in other embodiments. The coated fabric 122 comprises a fabric 124 that is surrounded on all sides by a coating 126.

The fabric 124 may comprise webbing, such as that formed by woven fabric. The webbing may comprise polyester webbing or other suitable materials. It is also contemplated that the fabric 124 may be formed of nylon webbing, polypropylene webbing, cotton webbing, elastic webbing, and the like. The coated fabric 122 has a thickness suitable to accommodate the connectors C1, C2. In some cases, the coated fabric 122 has a combined thickness T1 (fabric 124 and outer layers of coating 126) of from 0.038 to 0.047 inches, from 0.040 to 0.045 inches, or of 0.047 inches or less. In the embodiment shown, the coated fabric 122 has a thickness T1 of about 0.042 inches. The fabric 124 may have a thickness T2 of less than 0.047 inches, less than 0.046 inches, or less than 0.045 inches. In some cases, the fabric 124 has a thickness T2 of from 0.025 to 0.045 inches, from 0.030 to 0.040 inches, or from 0.030 to 0.035 inches. In the embodiment shown, the fabric 124 has a thickness T2 of about 0.032 inches. Other thicknesses are also contemplated.

The coating 126 may be applied to the fabric 124 by spraying, lamination, extrusion and/or co-extrusion processes, dipping the fabric 124 into the coating 126, moving the fabric 124 through the coating 126, molding the coating 126 onto the fabric 124, or the like. The coating 126 may comprise polymeric material, such as polyurethane, or other suitable materials to ease cleaning of the flexible restraint member 120. The coating 126 may be non-porous and/or non-fibrous. The coating 126 eases cleaning of the flexible restraint member 120 by providing a smooth, continuous, outer surface for wiping and thereby cleaning (as compared to the fabric 124). The coating 126 may be waterproof, water-resistant, and/or impervious to contaminants, such as dirt, grease, and body fluids. By coating the fabric 124 with polyurethane or other similar material, users are able to more easily wipe contaminants off the flexible restraint member 120 as compared to uncoated fabric, which tends to trap such contaminants. The coating 126 may have a cross-sectional thickness (as shown in FIG. 6) surrounding all sides of the fabric 124 of from 0.001 to 0.01 inches, from 0.004 to 0.008 inches, or of at least 0.005 inches. In the embodiment shown, the coating 126 has a thickness of about 0.005 inches. Other thicknesses are also contemplated.

Figure 7A:
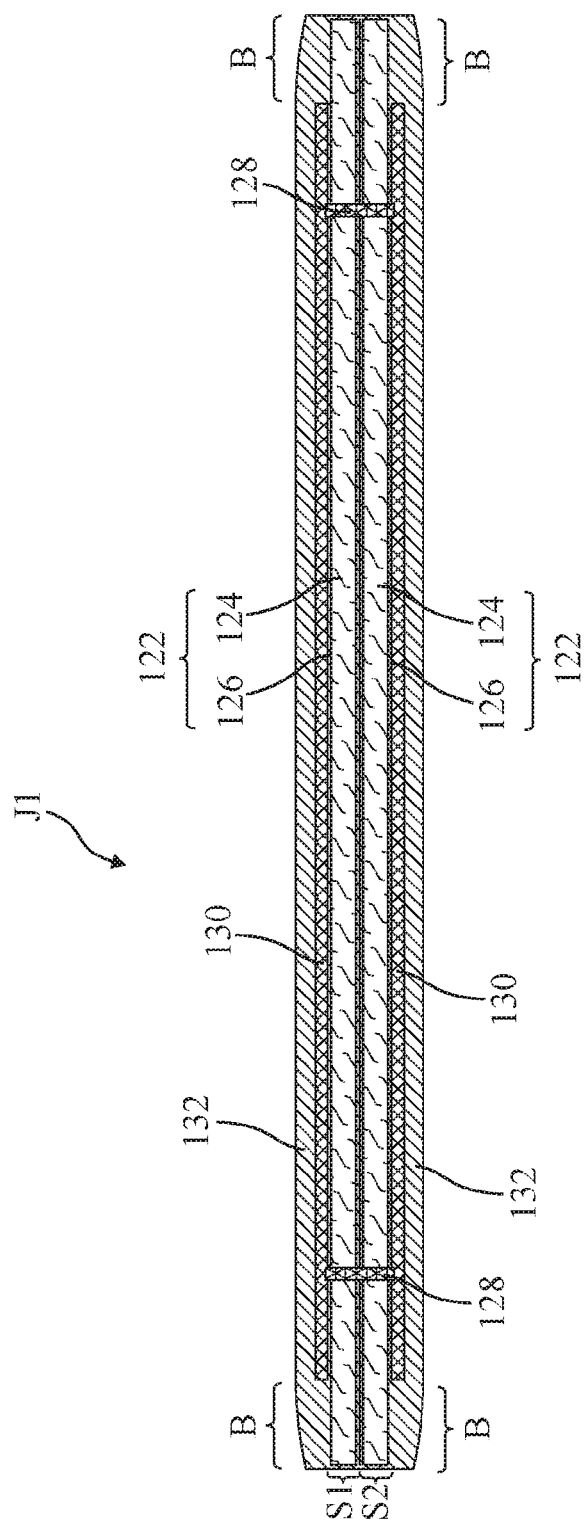
FIG. 7A is a cross-sectional view of the flexible restraint member taken along line 7A-7A of FIG. 5 illustrating layers of the flexible restraint member at the joint comprising coated fabric layers, stitches, adhesive, and covers.
Figure 7B:
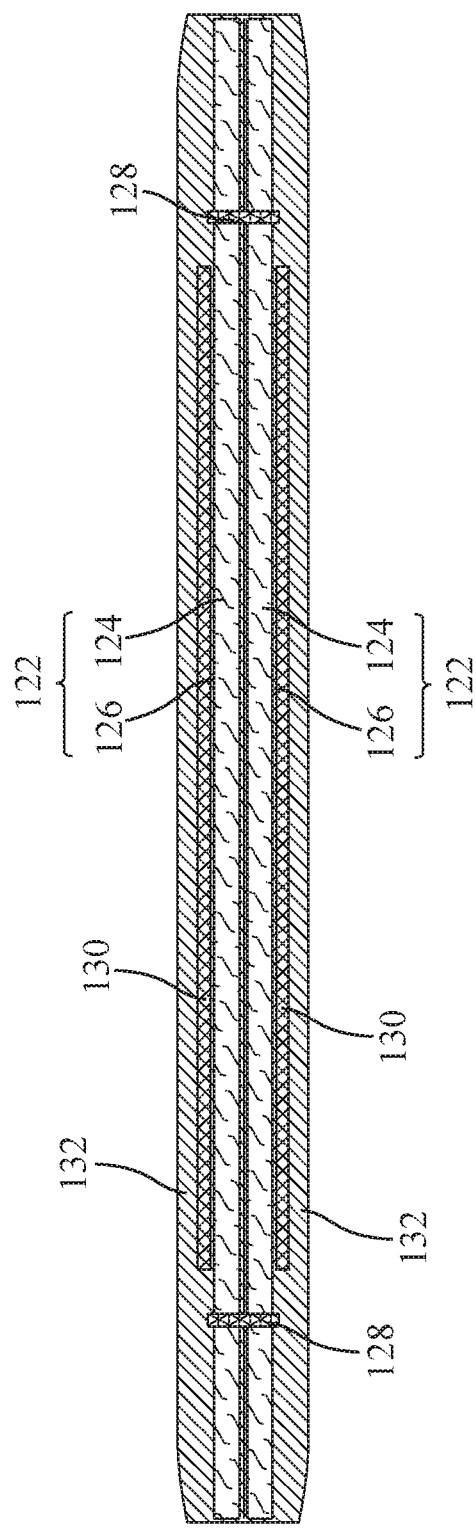
FIG. 7B is a cross-sectional view of the flexible restraint member, similar to FIG. 7A, but illustrating an alternative location for the adhesive.

Referring to FIG. 7A, a slice cross-sectional view through the flexible restraint member 120 at the first joint J1 is shown in detail. In the embodiment shown, the flexible restraint member 120 comprises multiple layers of material at the first joint J1: two layers of the coated fabric 122 secured to one another with stitches 128; adhesive 130; and covers 132. FIG. 7B is similar to FIG. 7A, but with the adhesive 130 located inside an outer periphery of the stitches 128. The first joint J1 is configured in a manner that prevents the ingress of dirt, grease, body fluids, and/or other contaminants into the fabric 124 and/or the stitches 128 at the first joint J1.

Figure 8:
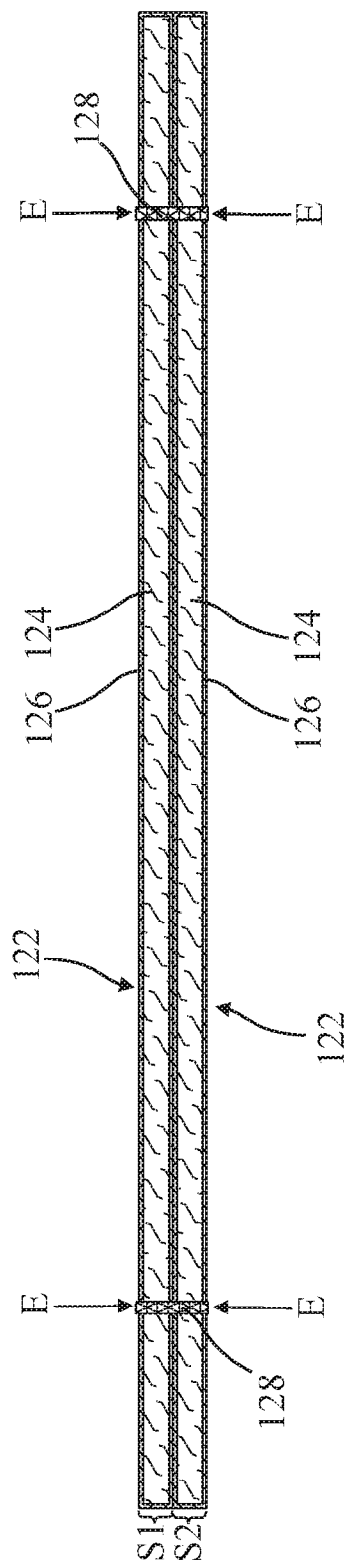
FIG. 8 is a cross-sectional view of the coated fabric layers joined together with the stitches, but prior to attaching the adhesive and the covers.

Referring to FIG. 8, during manufacture, two sections S1, S2 of the coated fabric 122 are first connected to one another with the stitches 128 to form the two layers of the coated fabric 122 at the first joint J1. The stitches 128 penetrate through the two layers of the coated fabric 122 to join them together such that the stitches 128 are exposed, as shown by the arrows E. The stitches 128 may comprise nylon thread or other suitable thread. In one embodiment, the nylon thread is sized 138/TEX 135/GOVT.FF. The stitches 128 may be provided in a stitching pattern such as a box X stitch, double W stitch, diamond stitch, horizontal diamond stitch, or any other suitable type of stitching pattern (see stitching pattern in FIG. 5A). Combinations of stitching patterns are also possible.

Figure 9:
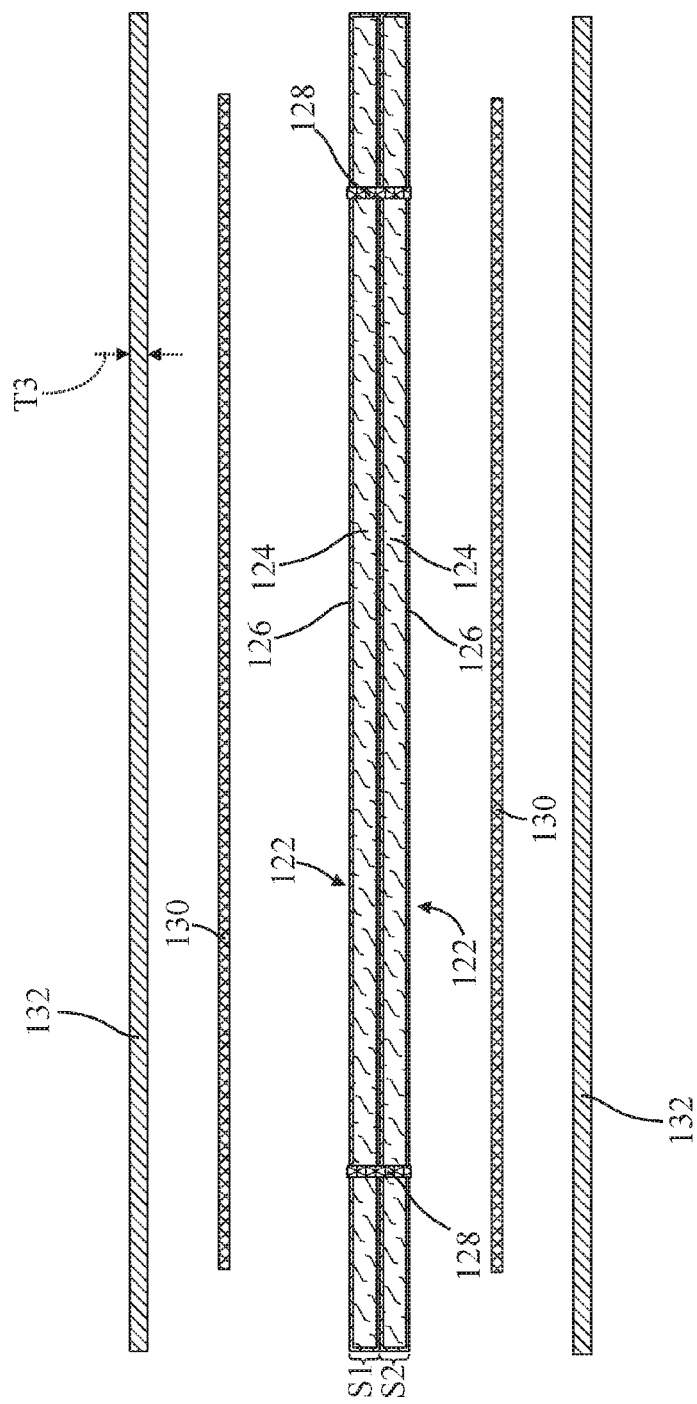
FIG. 9 is an exploded view showing the coated fabric layers joined together with the stitches and showing the adhesive and covers.
Figure 10:
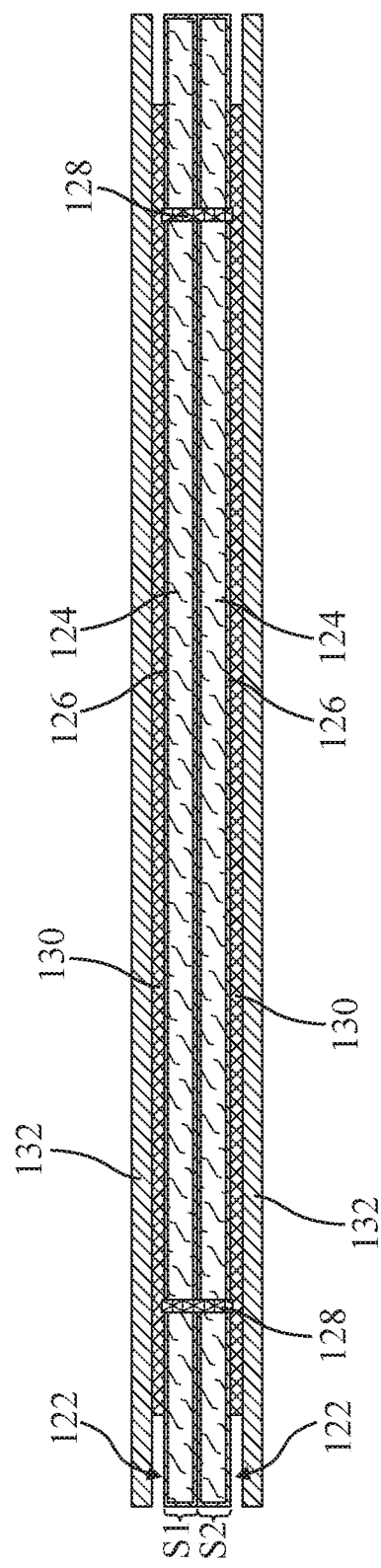
FIG. 10 is a cross-sectional view of the flexible restraint member at the joint prior to sealing the covers to the coated fabric layers along a periphery of the covers.

Referring to FIGS. 9 and 10, the adhesive 130 is applied over exposed surfaces of the sections S1, S2 of the coated fabric 122 once the sections S1, S2 are connected together with the stitches 128. The adhesive 130 may be applied to the sections S1, S2 inside an outer perimeter of the sections S1, S2. In this case, an outer perimeter of the adhesive 130 is spaced from the outer perimeter of the sections S1, S2. The adhesive 130 may be placed on the stitches 128 (see FIG. 7A) or away from the stitches 128 (see FIG. 7B). The adhesive may be applied as rectangular patches of film/tape on the sections S1, S2 and/or the stitches 128, sprayed onto the sections S1, S2 and/or the stitches 128, or otherwise applied to the sections S1, S2 and/or the stitches 128. In the embodiment shown, the adhesive comprises a double-sided self-adhesive tape, such as product no. 4965 manufactured by Tesa Tape, Inc. of Charlotte, N.C.

A covering is placed over the stitches 128 and the adhesive layers 130. In the embodiment shown, the covering comprises two separate covers 132 formed of rectangular patches sized to have the same width as the coated fabric 122 (other widths are also possible). In some cases, only a single cover 132 is used that wraps around to cover the stitches 128 on opposing surfaces. The covers 132 may be formed of urethane film or other suitable material. The covers 132 may comprise smooth, continuous, outer surfaces. The covers 132 may be non-porous and/or non-fibrous. The covers 132 may be waterproof, water-resistant, and/or impervious to contaminants to facilitate cleaning in the same manner as the coating 126.

As shown in FIG. 10, the adhesive 130 bonds to both the coated fabric 122 (e.g., the coating 126) on the sections S1, S2 and to the covers 132. This helps to reduce air pockets that may otherwise form between the coated fabric 122 and the covers 132 after the covers 132 are sealed to the coated fabric 122 in the manner described below. The covers 132 may have a thickness T3 (see FIG. 9) of from 0.002 to 0.02 inches, from 0.005 to 0.02 inches, or from 0.01 to 0.018 inches. In the embodiment shown, each of the covers 132 has a thickness of about 0.015 inches. Other thicknesses are also contemplated.

Referring briefly back to FIGS. 5A and 7A, the covers 132, once in position over the sections S1, S2, are sealed to the coating 126 in peripheral sealing bands B along the perimeters of the sections S1, S2. The bands B may have a width of from 0.03 to 0.2 inches, from 0.05 to 0.15 inches, or from 0.05 to 0.12 inches. One band B is shown in FIG. 5A on one side of the first joint J1, but a similar band B is also present on the opposite side of the first joint J1.

The covers 132 may be sealed along their entire outer peripheries to the sections S1, S2 by any suitable sealing method, such as ultrasonic welding, radio frequency (RF) welding, adhesive, other heat sealing methods, or the like. In some cases, both the covers 132 are sealed to the coating 126 simultaneously, for instance, by placing the entire construction of covers 132, adhesive 130, and sections S1, S2 in an RF welding die. In this case, the bands B represent weld locations. In other cases, such as when using adhesive, the covers 132 may be attached separately with adhesive placed along the bands B between the covers 132 and the coating 126 on the sections S1, S2.

The covers 132 may be sized to have outer peripheries that extend beyond the outer periphery of the stitches 128 so that the covers 132 completely cover and provide a barrier between the stitches 128 and possible outside contaminants. In the embodiment shown, the covers 132 are sealed to the coating 126 outside the outer periphery of the stitches 128 such that the covers 132 and coating 126 have melded together (see, e.g., FIG. 7A). By sealing the covers 132 outside the stitching pattern(s), the stitches 128 are able to move relative to one another inside the seal (e.g., inside the peripheral sealing band B).

Referring specifically to FIG. 5A, the manner in which the covers 132 are sealed may additionally involve heating and/or compressing the coated fabric 122 and covers 132 beyond the outer periphery of the covers 132 such that the covers 132 meld and integrate into the coating 126 of the coated fabric 122 to form a smooth and tapered transition from the covers 132 to adjacent sections of the coated fabric 122, as shown. This can also be used to seal a free end 140 of the coated fabric 122, which may have been cut during manufacturing and otherwise have exposed fabric 124. By heating one of the covers 132 and/or coating 126 to a suitable temperature, the material forming the cover 132 (e.g., urethane) and/or the coating 126 (e.g., polyurethane) is able to flow to a space adjacent the free end 140 to cover the free end 140, as shown. The covers 132, which are ultimately exposed to contaminants, are configured to provide a smoother, more continuous surface for cleaning and wiping, as compared to the stitches 128, which would otherwise be exposed without the covers 132.

Referring back to FIG. 5, the second joint J2 is formed in a similar manner as the first joint J1 described above except that the stitches 128 are made in a circular pattern and the covers 132 have a circular shape to cover the stitches 128. The covers 132, at the second joint J2, have a diameter greater than a diameter of the circular stitch pattern so that the covers 132 are able to be sealed to the coated fabric 122 outside an outer periphery of the circular stitch pattern. For some of the harness assemblies 102-114, a similar first joint J1 is utilized to create the connecting loop L. See, for example, the harness assemblies 102, 108, 110, 112, and 114 in FIG. 3B.

The third joint J3 is formed by sealing the other free end of the coated fabric 122 (opposite the free end 140) to an adjacent section, without any stitches or covers, but in a manner that also seals the other free end to eliminate any exposed fibers that may be present from the fabric 124. This is useful when the coated fabric 122 is manufactured in long lengths and cut into smaller lengths having two free ends with exposed fabric 124. In one embodiment, during assembly, the coating 126 at the other free end, and/or the coating 126 on the adjacent section to which the other free end is being attached, may be heated such that the coating 126 is flowable to seal off the fabric 124 at the other free end. When heating the coating 126 around the other free end, a smooth and tapered transition can be provided at the other free end of the coated fabric 122 with suitable dies, molds, etc. A similar third joint J3 is used to seal a free end of the coated fabric 122 in the harness assemblies 102, 110, and 114. In other embodiments, the free end of the coated fabric 122 can be sealed in other ways and/or using other suitable materials, such as adhesive, and the like. For instance, a separate cover (not shown) could be attached over the free end and adhered to the adjacent section to provide a barrier that protects any fabric 124 that would otherwise be exposed to contaminants.

As a result of the above-described construction of the flexible restraint member 120 and the joints J1, J2, J3 thereof, in the embodiment shown, there is no exposed fabric 124 or stitches 128 that would otherwise be susceptible to contamination and difficult to clean. In other words, the fabric 124 and stitches 128 are completely covered and sealed by the coating 126 and/or covers 132 such that the flexible restraint member 120 has generally smooth outer surfaces that can be easily cleaned after use. This will encourage continued reuse of the harness assemblies 102-114 and save costs associated with discarding soiled harness assemblies.

In some embodiments, the harness system 100 is configured to meet or exceed the requirements set forth in the SAE technical standards J3027 (which comprises SAE J2917 and SAE J2956). The harness system 100 may also be configured to meet or exceed the requirements set forth in the British Adopted European Standards BS EN 1789:2007 clause 4.5.9 and 5.4. One example of the harness system 100 that meets all the requirements of these standards is set forth below. In this example, each of the flexible restraint members 120 of the harness assemblies 102-114 comprises a single, continuous strap of coated fabric having a thickness of 0.042 inches and a width of 1.88 inches. The coated fabric 122 comprises polyester webbing with a polyurethane coating. The coating 126 has a thickness of 0.005 inches. The first and second joints J1, J2 are formed with the stitches 128 comprising nylon thread sized at 138/TEX 135/GOVT.FF. The stitches 128 are provided in a stitching pattern that comprises a box X stitch pattern (for the first joints J1) or circular pattern (for the second joints J2). The adhesive 130 applied onto the stitching pattern comprises double-sided self-adhesive tape, such as product no. 4965 manufactured by Tesa Tape, Inc. of Charlotte, N.C. The covers 132 comprise urethane film that is RF welded to the coated fabric 122. The covers 132 have a thickness of 0.015 inches.

It is to be appreciated that the terms "include," "includes," and "including" have the same meaning as the terms "comprise," "comprises," and "comprising."

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A harness assembly operable by a user for securing a patient to a patient transport apparatus, said harness assembly comprising:
   a connector; and
   a flexible restraint member coupled to said connector, said flexible restraint member comprising a fabric and a coating covering said fabric to protect said fabric from exposure to outside contaminants,
   said flexible restraint member comprising stitches securing first and second sections of said fabric together at a joint and a covering disposed over said stitches and attached to said first and second sections to provide a barrier that protects said stitches from exposure to outside contaminants at said joint.

2. The harness assembly of claim 1, wherein said covering is sealed to said sections.

3. The harness assembly of claim 2, wherein said covering is heat sealed to said coating at said sections.

4. The harness assembly of claim 1, wherein said covering comprises urethane.

5. The harness assembly of claim 1, wherein said covering comprises a first patch attached to said first section and a second patch attached to said second section.

6. The harness assembly of claim 1, wherein said fabric comprises polyester webbing.

7. The harness assembly of claim 6, wherein said fabric has a thickness of from 0.030 inches to 0.040 inches.

8. The harness assembly of claim 6, wherein said fabric has a thickness of less than 0.047 inches.

9. The harness assembly of claim 1, wherein said coating comprises polyurethane.

10. The harness assembly of claim 8, wherein said coating has a thickness of at least 0.005 inches.

11. The harness assembly of claim 1, wherein said coating and said covering have smooth outer surfaces to facilitate wiping of contaminants off said flexible restraint member.

12. The harness assembly of claim 1, comprising adhesive located between said covering and said coating.

13. The harness assembly of claim 1, wherein said fabric and said coating have a combined thickness of from 0.038 to 0.047 inches.

14. The harness assembly of claim 1, wherein said stitches are formed of nylon thread and are placed in a box X stitch pattern.

15. The harness assembly of claim 1, wherein said joint is located to provide a connecting loop configured to facilitate coupling of the harness assembly to the patient transport apparatus.

16. The harness assembly of claim 1, wherein said joint is located to provide a loop configured to engage said connector and secure said connector to said flexible restraint member.

17. The harness assembly of claim 1, wherein said joint secures a free end of said fabric, said covering being heat sealed to said coating at said joint such that said free end of said fabric is covered by at least one of said covering and said coating.

18. A harness assembly operable by a user for securing a patient to a patient transport apparatus, said harness assembly comprising:
a connector; and
a flexible restraint member coupled to said connector, said flexible restraint member comprising a fabric and a non-porous coating covering said fabric to protect said fabric from exposure to outside contaminants, said flexible restraint member comprising stitches securing first and second sections of said fabric together at a joint and a non-porous covering disposed over said stitches and attached to said first and second sections to provide a barrier that protects said stitches from exposure to outside contaminants at said joint.

19. A harness system operable by a user for securing a patient to a patient transport apparatus, said harness system comprising:
a plurality of harness assemblies configured to be coupled to the patient transport apparatus, each of said harness assemblies comprising:
a connector; and
a flexible restraint member coupled to said connector, said flexible restraint member comprising a fabric and a coating covering said fabric,
said flexible restraint member comprising stitches securing first and second sections of said fabric together at a joint and a covering disposed over said stitches and attached to said first and second sections to provide a barrier that protects said stitches from exposure to outside contaminants at said joint.

20. The harness system of claim 19, wherein two of said plurality of harness assemblies comprise shoulder harness assemblies configured to be attached to the patient transport apparatus and crossed over a torso of the patient in an X-configuration and said harness system is configured to meet the requirements of SAE technical standard J3027.

\* \* \* \* \*